United States Patent
Roe et al.

(10) Patent No.: US 10,039,782 B2
(45) Date of Patent: Aug. 7, 2018

(54) ONYCHOMYCOSIS TREATMENT APPARATUS AND METHOD

(71) Applicant: DeviceFarm Inc., Newark, CA (US)

(72) Inventors: Jeffrey N Roe, San Ramon, CA (US); Timothy C Grammer, Pleasant Hill, CA (US); Michael P O'Neil, Dublin, CA (US)

(73) Assignee: DeviceFarm, Inc., Newark, CA (US)

( * ) Notice: Subject to any disclaimer, the term of this patent is extended or adjusted under 35 U.S.C. 154(b) by 0 days.

(21) Appl. No.: 14/963,552

(22) Filed: Dec. 9, 2015

(65) Prior Publication Data

US 2016/0166607 A1 Jun. 16, 2016

Related U.S. Application Data

(60) Provisional application No. 62/089,945, filed on Dec. 10, 2014.

(51) Int. Cl.
| | |
|---|---|
| *A61K 33/04* | (2006.01) |
| *A61K 33/00* | (2006.01) |
| *A61K 31/02* | (2006.01) |
| *A61K 33/20* | (2006.01) |

(52) U.S. Cl.
CPC .............. *A61K 33/04* (2013.01); *A61K 31/02* (2013.01); *A61K 33/00* (2013.01); *A61K 33/20* (2013.01)

(58) Field of Classification Search
None
See application file for complete search history.

(56) References Cited

U.S. PATENT DOCUMENTS

| | | |
|---|---|---|
| 7,048,913 B2 | 5/2006 | Hexamer |
| 7,825,104 B2 | 11/2010 | Freeman et al. |
| 2005/0139808 A1 | 6/2005 | Alimi |
| 2007/0190082 A1 | 8/2007 | Shaffer et al. |
| 2008/0255498 A1 | 10/2008 | Houle |
| 2009/0143842 A1 | 6/2009 | Cumbie et al. |
| 2014/0213548 A1 | 7/2014 | Ulsh et al. |

FOREIGN PATENT DOCUMENTS

| | | |
|---|---|---|
| WO | 2003003989 A2 | 1/2003 |
| WO | 2014143412 A1 | 9/2014 |

OTHER PUBLICATIONS

Arndt, et al., Cold atmospheric plasma (CAP) changes gene expression of key molecules of the wound healing machinery and improves wound healing in vitro and in vivo, PLOS One, Nov. 12, 2013, pp. 1-9, vol. 8, issue 11.
Azzolini et al., Endophotocoagulation through perfluorodecalin in rabbit eyes, International Ophthalmology, 1994, vol. 18, pp. 33-36, Kluwer Academic Publishers.
Barrett, C.W., Skin Penetration, Journal of the Society of Cosmetic Chemists, 1969, vol. 20, pp. 487-499, Society of Cosmetic Chemists of Great Britian.
Bauer et al., Perfluorocarbon-tilled poly(lactide-co-gylcolide) nano- and microcapsules as artificial oxygen carriers for blood substitutes: a physico-chemical assessment, Journal of Microencapsulation, 2010, vol. 27, No. 2, pp. 122-132, Informa UK Ltd.
Davies, et al., Effect of the dose volume of perfluorocarbon when starting partial liquid ventilation, 2010, Journal of Paediatrics and Child Health, vol. 46, pp. 714-722, Paediatrics and Child Health Division (Royal Australasian College of Physicians).
Eliasson, et al., Nonequilibrium vol. plasma chemical processing, IEEE Transactions, Dec. 1991, vol. 19, issue 6, pp. 1063-1077.
Graves, The emerging role of reactive oxygen and nitrogen species in redox biology and some implications for plasma applications to medicine and biology, Journal of Physics D. Applied Physics, Jun. 13, 2012, pp. 1-42, vol. 45, IOP Publishing, UK and USA.
Heinlin, et al., Contact-free inactivation of T. rubrum and M. canis by cold atmospheric plasma treatment, 2012, 16 pages.
HPF8 Technical Sheet, High Purity Sterile Perfluoro-n-octane, 5 ml HPF 001-00, 2010, downloaded from www.alchimiasrl.com, Alchimia (Italy), 1 page.
HPF8 Technical Sheet, High Purity Sterile Perfluoro-n-octane, 7 ml HPF 002-00, 2010, downloaded from www.alchimiasrl.com, Alchimia (Italy), 1 page.
HPF10 Technical Sheet, High Purity Sterile Perfluorodecalin, 5 ml, HPF 003-00, 2010, downloaded from www.alchimiasrl.com, Alchimia (Italy), 1 page.
HPF10 Technical Sheet, High Purity Sterile Perfluorodecalin, 7 ml, HPF 004-00, 2010, downloaded from www.alchimiasrl.com, Alchimia (Italy), 1 page.
HPF8 Technical Sheet, High Purity Sterile Perfluoro-n-octane, in Pre-filled Syringe, 5 ml, HPF 019-00, 2010, downloaded from www.alchimiasrl.com, Alchimia (Italy), 1 page.
HPF8 Technical Sheet, High Purity Sterile Perfluoro-n-octane, in Pre-filled Syringe, 7 ml, HPF 020-00, 2010, downloaded from www.alchimiasrl.com, Alchimia (Italy), 1 page.
HPF10 Technical Sheet, High Purity Sterile Perfluorodecalin, in Pre-Filled Syringe, 5 ml, HPF 021-00, 2010, downloaded from www.alchimiasrl.com, Alchimia (Italy), 1 page.
HPF10 Technical Sheet, High Purity Sterile Perfluorodecalin, in Pre-Filled Syringe, 7 ml, HPF 022-00, 2010, downloaded from www.alchimiasrl.com, Alchimia (Italy), 1 page.
HPF10 Perfluorodecalin Withdrawal & Injection Kit Technical Sheet, High Purity Sterile Perfluorodecalin, 7 ml, HPF 308-00, Dec. 14, 2010, downloaded from www.alchimiasrl.com, Alchimia (Italy), 1 page.
Isbary, et al., Successful and safe use of 2 min cold atmospheric argon plasma in chronic wounds: results of a randomized controlled trial, British Journal of Dermatology, 2012, pp. 404-410, vol. 167, British Association of Dermatologists.

(Continued)

*Primary Examiner* — Dennis J Parad
(74) *Attorney, Agent, or Firm* — Joel Douglas; Shirley A. Recipon (57) ABSTRACT

A system and method includes delivery of a redox gas solution to treat onychomycosis, wherein the redox gas solution comprises a reactive species dissolved in a perfluorocarbon liquid, and wherein the reactive species may include, alone or in combination, one or more of reactive oxygen, reactive nitrogen, reactive chlorine, or reactive bromine species, and the perfluorocarbon liquid may include perfluorodecalin.

28 Claims, 4 Drawing Sheets

(56) References Cited

OTHER PUBLICATIONS

Isbary, et al., Cold atmospheric plasma for local infection control and subsequent pain reduction in a patient with chronic post-operative ear infection, New Microbes and New Infections, Dec. 2013, pp. 41-43, vol. 1, No. 3, John Wiley & Sons.

Isbary, et al., Ex vivo human skin experiments for the evaluation of safety of new cold atmospheric plasma devices, Clinical Plasma Medicine, 2013, pp. 36-44, vol. 1, Elsevier GmbH.

Isbary, et al., Cold atmospheric plasma devices for medical issues, Expert Rev. Med. Dev., 2013, pp. 367-377, vol. 10, No. 3, Expert Reviews Ltd.

Jeng, et al., Effects of perfluorochemical evaporative properties on oxygenation during partial liquid ventilation, 2006, Pediatrics international, vol. 48, pp. 608-615.

Kogelschatz, Dielectric-barrier discharges: their history, discharge physics, and industrial applications, Mar. 2003, pp. 1-46, vol. 23, No. 1, Plenum Publishing Corporation.

Kogelschatz, et al., Ozone generation from oxygen and air: discharge physics and reaction mechanisms, Ozone Science and Engineering, 1988, pp. 367-378, vol. 10, International Ozone Association, USA.

Kong, et al., Plasma medicine: an introductory review, New Journal of Physics, Nov. 26, 2009, pp. 1-35, vol. 11, IOP Publishing Ltd.

Koritzer, et al., Restoration of Sensitivity in chemo-resistant glioma cells by cold atmospheric plasma, PLOS One, May 21, 2013, 10 pages, PLOS One.

Krafft, Fluorocarbons and fluorinated amphiphiles in drug delivery and biomedical research, 2001, Advanced Drug Delivery Reviews, vol. 47, pp. 209-228, Elsevier Science B.V.

Li, et al., In vivo skin treatmentusing two portable plasma devices: comparison of a direct and an indirect cold atmospheric plasma treatment, Clinical Plasma Medicine, 2013, pp. 35-39, vol. 1, Elsevier GmbH.

Libinvest Cosmetics, Perfluorodecalin, available online at http://www.libinvest.com/en/raw_materials.php?id=15&lang=en, date of first publication unknown, printed on 9 pages on Mar. 28, 2012.

Littlejohn, et al., A Simple Method for Imaging *Arabidopsis* Leaves Using Perfluorodecalin as an Infiltrative Imaging Medium, Jan. 16, 2012, Journal of Visualized Experiments, Issue 59, e3394, pp. 1-4.

Littlejohn et al., Perfluorodecalin improves in-vivo confocal depth resolution in air-filled tissues, 6 pages, printed tom the Illuminated Plant Cell website, http://www.illuminatedcell.com/improved-imaging.html on Mar. 23, 2012, first publication date unknown.

Littlejohn, et al., A Simple Method for Imaging *Arabidopsis* Leaves Using Perfluorodecalin as an Infiltrative Imaging Medium, Journal of Visualized Experiments, vol. 59, e3394, pp. 1-4, with a video component of the article reported found at http://www.jove.com/video/3394/.

Littlejohn, et al., Perfluorodecalin enhances in vivo confocal microscopy resolution of *Arabidopsis thaliana* mesophyll, New Phytologist, 2010, pp. 1018-1025, vol. 186, New Phytologist Trust.

Lowe, Engineering Blood: Synthetic Substitutes from Fluorinated Compounds, 2003, Tissue Engineering, vol. 9, No. 3, pp. 389-399, with 2 additional pages reporting listings citing this article.

Lowe, Second-Generation Perfluorocarbon Emulsion Blood Substitutes, 2000, Art. Cells, Blood Subs., and Immob. Biotech., vol. 28(1), pp. 25-38, Marcel Dekker. Inc.

Maisch, et al., Contact-free cold atmospheric plasma treatment of deinococcus radiodurans, J. Ind. Microbiol. Biotechnol., May 15, 2012, 10 pages, Springer.

Maisch, et al., Decolonisation of MRSA, *S. aureus* and *E. coli* by cold-atmospheric plasma using a porcine skin model in vitro, PLOS One, Apr. 27, 2012, pp. 1-9, vol. 7, issue 4, PLOS One.

Mitra, et al., Inactivation of surface-borne microorganisms and increased germination of seed specimen by cold atmospheric plasma, Food and Bioprocess Technology, May 26, 2013, pp. 645-653, vol. 7, issue 3, Springer.

Morfill, et al., Nosocomial infections—a new approach towards preventive medicine using plasmas, New Journal of Physics, Nov. 26, 2009, pp. 1-10, vol. 11, IOP Publishing Ltd.

Material Safety Data Sheet Perfluorodecalin MSDS, available at www.sciencelab.com and obtained from website on Apr. 19, 2012, reported created Oct. 10, 2005, date unknown, 5 pages.

Pavlovich, et al., Quantification of air plasma chemistry for surface disinfection, Plasma Sources Science and Technology, Oct. 20, 2014, pp. 1-10, vol. 23, IOP Publishing, UK.

Pavlovich, Chapter 5: Ozone correlates with antibacterial effects from indirect air dielectric barrier discharge treatment of water, 2013, pp. 44-60.

Pavlovich, et al., Effect of discharge parameters and surface characteristics on ambient-gas plasma disinfection, Plasma Processes and Polymers, 2013, pp. 69-76, vol. 10, Wiley-VCH Verlag Gmbh & Co.

Sakiyama, et al., Plasma chemistry model of surface microdischarge in humid air and dynamics of reactive neutral species, Journal of Physics D. Applied Physics, Oct. 1, 2012, pp. 1-19, vol. 45, IOP Publishing Ltd., UK and USA.

Shimizu, et al., The dynamics of ozone generation and mode transition in air surface micro-discharge plasma at atmospheric pressure, New Journal of Physics, Oct. 17, 2012, pp. 1-11, vol. 14, IOP Publishing.

Stoilov, Fluorocarbons as Volatile Surfactants, 1998, Langmuir, vol. 14, No. 20, pp. 5685-5690, American Chemical Society.

Traylor, et al., Long-term antibacterial efficacy of air plasma-activated water, Journal of Physics D. Applied Physics, Nov. 4, 2011, pp. 1-4, vol. 44, IOP Publishing Ltd., UK and USA.

International Search Report and Written Opinion of the International Searching Authority, PCT/US2015/064666, dated Feb. 19, 2016, 11 pages.

https://en.wikipedia.org/wiki!Gas_exchange, printed on Oct. 24, 2016, pp. 1-4.

https://www.boundless.com/chemistry/textbooks/boundless-chemistry-textbook/thermochemistry-6/enthalpy-59/exothermic-and-endothermic-processes-277-3716/, Boundless Open Textbook, Exothermic and Endothermic Processes, printed on Oct. 24, 2016, pp. 1-11.

Johnson, JL, et al., In Vitro Comparison of Dodecafluoropentane (DDFP), Perfluoroddecalin (PFD), and Periluoroctylbromide (PFOB) in the Facilitation of Oxygen Exchange. Artificial Cells, Blood Substitutes, and Biotechnology, vol. 37, pp. 156-162, 2009.

Tamimi, F, et al. Pertluorodecalin and Bone Regeneration, European Cells and materials, vol. 25; pp. 22-36 (2013).

Dias A.M.A.; et al., Solubility of oxygen in liquid perfluorocarbons, Fluid Phase Equilibria, vol. 222; pp. 325-330 (2004).

PCT/US2015/064666 International Preliminary Report on Patentability dated Jun. 13, 2017.

Notification of Transmittal of the International Search Report a nd the Written Opinion of the International Searching Authority, or the Declaration (PCT Rule 44.I) dated May 24, 2018.

ONYCHOMYCOSIS TREATMENT APPARATUS AND METHOD

RELATED APPLICATIONS

This application is related to and claims priority from U.S. provisional patent application Ser. No. 62/089,945, filed Dec. 10, 2014, entitled Onychomycosis Treatment Apparatus and Method, which is hereby incorporated by reference herein for all purposes.

STATEMENT REGARDING FEDERALLY SPONSORED RESEARCH OR DEVELOPMENT

This invention was made with government support under NSF Award ID 1343994 and NIH Award ID 1R43GM112196-01 awarded by the National Science Foundation and the National Institute of Health. The government has certain rights in the invention.

FIELD OF THE DISCLOSURE

The invention in one aspect relates generally to a system and method for the treatment of onychomycosis.

BACKGROUND

Onychomycosis (also known as "dermatophytic onychomycosis," or "tinea unguium") is a fungal infection of the nail. It is the most common disease of the nails and constitutes about half of all nail abnormalities. This condition may affect toenails or fingernails, but toenail infections are particularly common. It occurs in about 10% of the adult population.

The most common symptom of a fungal nail infection is the nail becoming thickened and discolored. As the infection progresses the nail can become brittle, with pieces breaking off or coming away from the toe or finger completely. If left untreated, the skin can become inflamed and painful underneath and around the nail. There may also be white or yellow patches on the nail bed or scaly skin next to the nail, and an odor may result. There is usually no pain or other bodily symptoms, unless the disease is severe. People with onychomycosis may experience significant psychosocial problems due to the appearance of the nail, particularly when fingers—which usually are always visible—rather than toenails are affected.

Dermatophytids are fungus-free skin lesions that sometimes form as a result of a fungus infection in another part of the body. This could take the form of a rash or itch in an area of the body that is not infected with the fungus. Dermatophytids can be thought of as an allergic reaction to the fungus.

The causative pathogens of onychomycosis include dermatophytes, *Candida*, and non-dermatophytic molds. Dermatophytes are the fungi most commonly responsible for onychomycosis in the temperate western countries; while *Candida* and nondermatophytic molds are more frequently involved in the tropics and subtropics with a hot and humid climate.

*Trichophyton rubrum* is the most common dermatophyte involved in onychomycosis. Other dermatophytes that may be involved are *T. interdigitale, Epidermophyton floccosum, T. violaceum, Microsporum gypseum, T. tonsurans,* and *T. soudanense*. A common outdated name that may still be reported by is *Trichophyton mentagrophytes* for *T. interdigitale*. The name *T. mentagrophytes* is now restricted to the agent of favus skin infection of the mouse; though this fungus may be transmitted from mice and their danders to humans, it generally infects skin and not nails.

Other causative pathogens include *Candida* and nondermatophytic molds, in particular members of the mold generation *Scytalidium* (name recently changed to *Neoscytalidium*), *Scopulariopsis*, and *Aspergillus*. *Candida* mainly causes fingernail onychomycosis in people whose hands are often submerged in water. *Scytalidium* mainly affects people in the tropics, though it persists if they later move to areas of temperate climate.

All causative pathogens are susceptible to certain toxic gasses, such as ozone, oxides of nitrogen, and similar reactive materials. It is understood that fluid and solid materials may also have similar beneficial anti-pathogenic properties. However, there are a number of problems associated with the use of such anti-pathogenic substances to treat onychomycosis. The nail bed itself can act as a barrier to curative gasses and beneficial anti-pathogenic substances. Thus, there remains a need for a system and method for the treatment of onychomycosis that permits substances to traverse, surround and/or enter the nail bed and similar physiological structures for a beneficial effect.

There also remains an unmet medical need for a topical treatment device and treatment method for onychomycosis that is effective, requiring short treatment times and without the undesirable side effects of the prior art. Many chemical compounds exhibit antifungal (fungistatic or fungicidal) properties, and can be incorporated into creams, lotions, gels, solutions and the like. However, antifungal compounds applied topically (i.e., directly to the nail) do not adequately and consistently penetrate the nail bed to kill the fungus at its source, and thus are not consistently effective.

Thus, an additional or improved apparatus and method for treating onychomycosis is desirable.

SUMMARY

The present disclosure provides a system and method that includes delivery of a redox gas solution to treat onychomycosis, wherein the redox gas solution comprises a reactive species dissolved in a perfluorocarbon liquid.

In one exemplary embodiment, the reactive species may include, alone or in combination, one or more of reactive oxygen, reactive nitrogen, reactive chlorine, or reactive bromine species. The perfluorocarbon liquid may include perfluorodecalin.

Other benefits and advantages of the present disclosure will be appreciated from the following detailed description.

DESCRIPTION OF THE DRAWINGS

Exemplary embodiments of a system and method are shown in the accompanying drawings.

DETAILED DESCRIPTION

Embodiments of the invention and various alternatives are described. Those skilled in the art will recognize, given the teachings herein, that numerous alternatives and equivalents exist which do not depart from the invention. It is therefore intended that the invention not be limited by the description set forth herein or below.

One or more specific embodiments of the system and method will be described below. These described embodiments are only exemplary of the present disclosure. Additionally, in an effort to provide a concise description of these exemplary embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Further, for clarity and convenience only, and without limitation, the disclosure (including the drawings) sets forth exemplary representations of only certain aspects of events and/or circumstances related to this disclosure. Those skilled in the art will recognize, given the teachings herein, additional such aspects, events and/or circumstances related to this disclosure, e.g., additional elements of the devices described; events occurring related to onychomycosis treatment; etc. Such aspects related to this disclosure do not depart from the invention, and it is therefore intended that the invention not be limited by the certain aspects set forth of the events and circumstances related to this disclosure.

Figure 1:
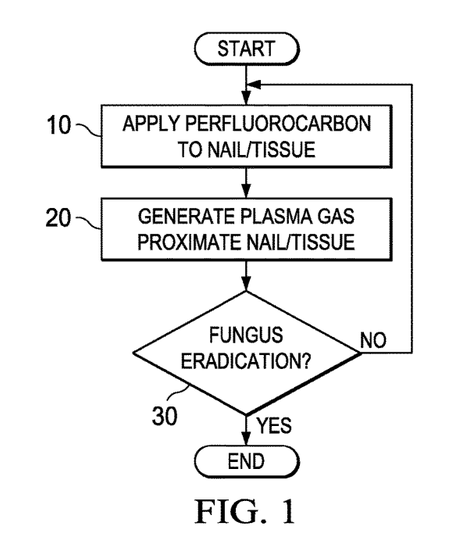
FIG. 1 is an illustration by flowchart of an exemplary method in accordance with the disclosure.

Turning now to the drawings, the figures show an exemplary treatment system and method. As described in FIG. 1, the system provides delivery of a redox gas solution to treat onychomycosis, wherein the redox gas solution comprises a reactive species dissolved in a perfluorocarbon liquid. The perfluorocarbon liquid is applied at step 10 to the nail/tissue. Then, at step 20, a plasma gas is generated proximate the nail/tissue. The plasma gas forms reactive species that dissolve in the perfluorocarbon liquid to form a redox gas solution. The process may repeat or continue until sufficient redox gas solution is produced to eradicate nail/tissue fungus. See step 30.

In one exemplary embodiment, the reactive species may include, alone or in combination, one or more of reactive oxygen, reactive nitrogen, reactive chlorine, or reactive bromine species. The reactive species may be formed through use of a non-thermal plasma device, or otherwise be provided.

Figure 2:
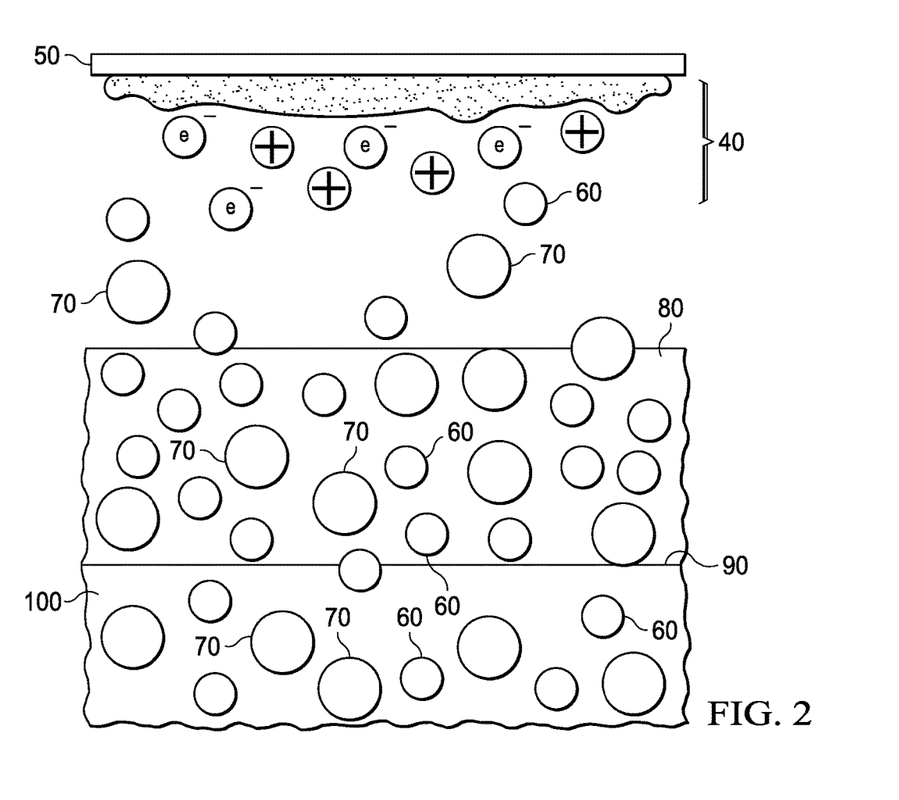
FIG. 2 is a cross-sectional view of a portion of an exemplary system in accordance with the disclosure.

As shown in FIG. 2, a plasma 40 may be formed proximate a ground electrode 50. The plasma forms reactive species 60, 70. The reactive species 60, 70 dissolve in a perfluorocarbon liquid 80 applied to the surface 90 of nail/tissue 100. The redox gas solution including reactive species 60, 70 diffuses into the nail/tissue bed to eradicate fungus located therein. As shown in FIG. 2, the plasma generating device includes a ground electrode 50. In addition, the device includes sufficiently high voltage pulses applied between two electrodes, one of which is the ground electrode 50, where at least one of the electrodes is insulated for plasma generation (not shown for clarity in FIG. 2).

Perfluorocarbon Liquids (PFCs)/Other Facilitators

The perfluorocarbon liquid may include perfluorodecalin. Perfluorodecalin and other suitable perfluorocarbon liquids have desirable wetting, gas absorption and diffusion properties.

Perfluorocarbons (PFCs), fluorocarbons, or perfluorochemicals (terms which may be used interchangeably) liquids are formally derived from liquid hydrocarbons by replacing all the hydrogen atoms with fluorine atoms. This class of chemical compounds is characterized by its property to be extremely inert—chemically, biologically, and physiologically—due to the remarkable stability of the C—F bonds. The C—F bond is the strongest bond encountered in organic chemistry, and its strength is further increased when several fluorine atoms are present on the same carbon atom. The presence of fluorine even reinforces the strength of the C—C bonds.

PFC liquids generally are clear, colorless, odorless, non-conducting, and nonflammable. They are approximately twice as dense as water, and generally are capable of dissolving large amounts of physiologically important gases. For their gas uptake function, PFCs act only as a carrier of the gasses and do not react with the gas or produce the gases. PFCs are generally very chemically stable compounds that are not metabolized in body tissues. They are physiologically inert as there is no enzyme system capable of modifying liquid PFCs, neither metabolically nor catabolically. Liquid PFCs are both hydrophobic and lipophobic, i.e., they are immiscible both with water and lipophilic liquids and generally form emulsions with them.

PFCs are used in a variety of industries. They were first synthesized in the 1920s and developed for industry in the 1940s. PFCs are currently being used in retinal detachment surgery, liquid ventilation therapy for the lungs, as a blood substitute and as ultrasound and radiological imaging agents. They are used in both cosmetics and paints to facilitate easier product spreading and in textile manufacturing as a fabric protector.

The term "perfluorocarbon liquid" or "PFC liquid" as used herein may include organic compounds in which all (or essentially all) of the hydrogen atoms are replaced with fluorine atoms. Representative perfluorinated liquids include cyclic and non-cyclic perfluoroalkanes, cyclic and non-cyclic perfluoroamines, cyclic and noncyclic perfluoroethers, cyclic and non-cyclic perfluoroaminoethers, and any mixtures thereof.

Specific examples of perfluorinated liquids include the following: perfluoropentane, perfluorohexane, perfluoroheptane, perfluorooctane, perfluorodecalin, perfluoromethylcyclohexane, perfluorotributyl amine, perfluorotriamyl amine, perfluoro-N-methylmorpholine, perfluoro-Nethylmorpholine, perfluoroisopropyl morpholine, perfluoro-N-methyl pyrrolidine, perfluoro-1,2 is(trifluoromethyl)hexafluorocyclobutane, perfluoro-2- butyltetrahydrofuran, perfluorotriethylamine, perfluorodibutyl ether, and mixtures of these and other perfluorinated liquids.

Perfluorocarbons in general improve gas exchange and are a desirable medium to carry redox gases. PFC at one atmosphere of pressure can carry 20 times more oxygen than saline will hold. PFCs are low viscosity surfactants that may lower the surface tension on the nail, so the PFC may spread uniformly and quickly over the nail structure. The low surface tension contributes to improved wetting of the surfaces. The surface tensions of PFC's are generally less than 20 dynes/cm and usually between 10 to 20 dynes/cm when measured at 25° C. When used in lung injury for ARDS patients, surface tension in the lung is noted to be 67 to 75 dynes/cm. In a lung with PFC, the surface tension is only 18 dynes/cm, which helps prevent alveolar collapse and reduces alveolar opening pressures.

PFCs may displace water and circulate to those areas where gas exchange is diminished. PFCs also may wash out debris if the debris is lighter than the PFC used. PFCs are not taken up by the body and do not break down into toxic metabolites.

Perfluorocarbon liquids may be compounds containing a high level of carbon-bound fluorine that are liquid at or below 106° F. These fluorinated fluids may be capable of dissolving a substantial amount of a redox gas at operating conditions, typically in a temperature range from about 0° C. to about 50° C. The perfluorocarbon liquid may be converted in whole or in part to a redox gas solution before topical application by dissolving the reactive gaseous species into perfluorocarbon liquid at the manufacturing facility and delivering the topical composition to the customer in a usable form such that the customer can apply the solution to the infected area as a treatment. In one exemplary embodiment, PFC fluids may dissolve at least 500 mL of gaseous chlorine per 100 mL of fluid at 1 atm and 25° C. In another exemplary embodiment, the PFC fluids may dissolve at least 1200 mL of gaseous chlorine at 1 atm and 25° C. The oxidizing gas solutions used in the described methods may be saturated with a desired oxidizing gas. In another example, the concentration of ozone in the PFC may be greater than 1 ppm but less than 500 ppm. Fluorinert™ Fluids, product bulletin 98-0211-8301-1(65.05)R, issued 5/95, available from 3M Co., St. Paul, Minn., provides the solubility of many oxidizing gases in Fluorinert™ Electronic Fluids.

Other perfluorocarbons that may be used include, by way of example, perfluorocarbons such as fluoroheptanes, fluorocycloheptanes, fluoromethylcycloheptanes, fluorohexanes, fluorocyclohexanes, fluoropentanes, fluorocyclopentanes, fluoromethylcyclopentanes, fluorodimethylcyclopentanes, fluoromethylcyclobutanes, fluorodimethylcyclobutanes, fluorotrimethylcyclobutanes, fluorobutanes, fluorocyclobutanse, fluoropropanes, fluoroethers, fluoropolyethers, fluorotributylamines, fluorotriethylamines, perfluorohexanes, perfluoropentanes, perfluorobutanes, perfluoropropanes, sulfur hexafluoride, Methylperfluorobutylether (GransilSiW 7100) or Perfluoro (tert-butylcyclohexane). Also mixtures of perfluorocarbons could also be utilized in this invention that combine different perfluorocarbons and perfluorocarbon compositions such as PFC emulsions or PFC gels.

Other liquids may fulfill the mechanism of penetration enhancer/gas carrier and could concentrate the antifungal species from the plasma. In addition to PFCs, alternative molecules that both concentrate and promote gas exchange may be used and include, but are not limited to, neuroglobin, apomyoglobin, hemoglobin, myoglobin, and synthetic blood or blood substitutes such as respirocytes.

In another exemplary embodiment, the perfluorocarbon or other liquid may include a co-solvent to improve as desired specific physical properties of the fluid. A semifluorinated alkane (SFA) that has a non-fluorinated hydrocarbon segment may be added to a PFC liquid. In another exemplary embodiment, the liquid composition may comprise the combination of more than one PFC and/or more than one SFA. It may be useful to combine PFCs and SFAs, for example, to achieve a particular desired target property, such as a certain density, viscosity, lipophilicity or soluble capacity for a particular active ingredient such as a dye. The SFA may be essentially non-reactive with the redox gas. The SFA also may not reduce the solubility of the redox gas in the PFC. In one exemplary embodiment, one or more useful SFAs may be selected from a group of SFAs including $F_4H_5$, $F_4H_6$, $F_4H_8$, $F_6H_6$ and $F_6H_8$.

Redox Gas Solutions

In one exemplary embodiment, the perfluorocarbon liquid absorbs anti-pathogenic substances generated by a plasma-generating device. See, e.g., FIG. 2. In one exemplary aspect, onychomycosis treatment is enhanced using a solution containing gaseous reactive oxygen or reactive nitrogen or reactive chlorine/bromine species that are dissolved in a perfluorocarbon liquid.

For convenience only, and without limitation, a solution containing gaseous reactive oxygen or reactive nitrogen or reactive chlorine/bromine species dissolved in a perfluorocarbon liquid shall be referred to herein as a "redox gas solution."

In accordance with another exemplary embodiment, an onychomycosis treatment system and method includes a topical composition to overcome one or more disadvantages of current topical fungal treatments. In one aspect, the topical composition may include a redox gas solution.

In another aspect, a further exemplary embodiment provides a method of treating fungal infections like onychomycosis comprising contacting a skin or nail surface with a perfluorocarbon liquid, and converting at least a portion of the perfluorocarbon liquid into a redox gas solution. In another aspect, such method includes the step of dissolving a redox gas in a perfluorocarbon liquid proximate the site of a fungal infection like onychomycosis to be treated. In another exemplary embodiment, the redox gas is formed during a non-thermal plasma treatment step.

In accordance with another exemplary embodiment, first and second treatment vectors for a fungal infection like onychomycosis are provided, wherein the first vector includes a redox gas formed as a result of a non-thermal plasma treatment step, and the second vector includes a redox gas solution.

Plasma-Generating Devices

In accordance with one exemplary embodiment, a plasma-generating device may create antimicrobial plasma species proximate a nail or skin area to be treated.

As used herein, the term "antimicrobial" means tending to destroy microbes, prevent their development, or inhibit their pathogenic action, and includes reference to, without limitation, antibacterial and antifungal properties.

Plasma is a gas-like phase of matter that typically contains many more reactive chemistry species than gas. A plasma-generating device turns electrical energy and a preselected gas (typically air, argon or helium) into electric fields, energetic electrons and favorable chemistry for antimicrobial therapy.

There are multiple technologies that have been used for plasma-generating devices at atmospheric pressure and temperatures. Non-thermal plasma gas at atmospheric pressure have been generated by microwave-induced plasma systems, dielectric barrier discharge (DBD), corona discharge, gliding arc discharge, and atmospheric pressure plasma jet. U.S. Pat. No. 7,572,998 is hereby expressly incorporated by reference herein in its entirety for all purposes. The '998 patent describes some representative, but not exclusive, plasma generators that may be useful.

Figure 4:
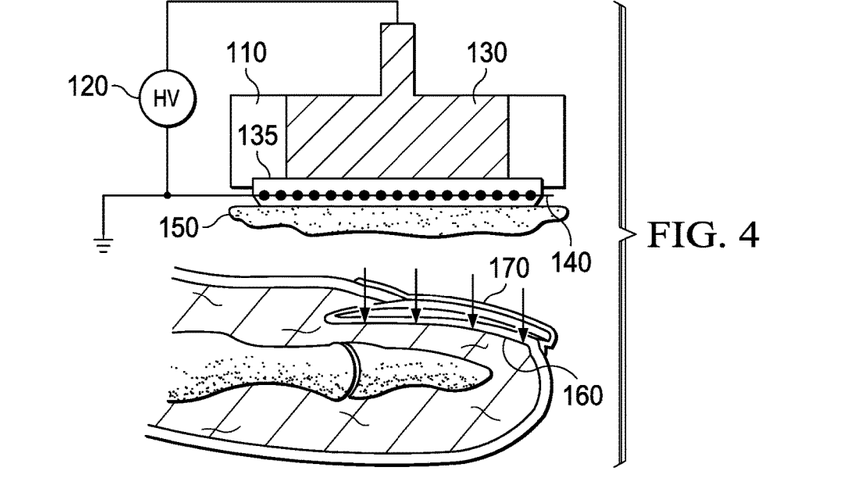
FIG. 4 is a partial schematic view of an exemplary plasma generating device proximate nail/tissue to which a perfluorocarbon liquid has been applied in accordance with the disclosure.

As shown in FIG. 4, the plasma-generating device 110 is electrically connected to both a power supply 120 and electrical control circuit to control both the duration and intensity of the plasma gas effluent 150. The electrical system may generate a high-voltage alternating current, typically between 2 to 20 kV at a frequency between 1 to 60 kHz. The power consumption may range from 0.05 W to 10.0 W. The high voltage electrode 130 may include a cylindrical copper block covered by a thin quartz plate 135 (e.g., approximately 1 mm in thickness). A stainless-steel woven wire mesh may be positioned next to the quartz plate 135 and used as the ground electrode 140. A wire diameter of 0.5 mm and mesh density of 8×8 meshes per $cm^2$, for example, may be used.

A variation of the dielectric barrier discharge (DBD), the surface micro-discharge (SMD) may prove advantageous as the plasma-generating device in applications for igniting a stable plasma at ambient conditions. A SMD is a configuration of a DBD where the high voltage electrode is separated from a grounded electrode by a dielectric layer. The term dielectric barrier discharges may be used because current is forced through an electrical insulator (e.g., glass) to create a plasma. In a SMD, the charged particles may be confined to a plasma generation region around the grounded metal electrode. A SMD may be a desirable source of reactive chemical species for several reasons: the treated body part is electrically isolated from high-voltage electrode due to ground electrode; the discharges are non-thermal, increasing adjacent gas temperature slightly, e.g., by only a few degrees; devices can be scaled simply, e.g., by changing electrode size and input power; and the discharges may operate in ambient air, e.g., without requiring a noble gas mixture. SMD devices have been further described in a series of articles by Graves et al. and Morfill et al.

Multiple reactive oxygen species (ROS) and reactive nitrogen species (RNS) may be generated in a non-thermal plasma. The active content of the plasma effluent at the treatment surface may include, for example, singlet oxygen ($1O_2$), hydroxide (OH), hydrogen peroxide ($H_2O_2$), ozone ($O_3$), nitrous oxide ($N_2O$), nitrogen dioxide ($NO_2$) and other excited molecules of air constituents that includes other reactive nitrogen and reactive oxygen species such as $HNO_2$, $NO_3$, $HNO_3$ and $N_2O_5$. Side reactions with these chemistries also may generate beneficial liquids and solids as the nail keratin and water in the nail can maintain antifungal properties long after the treatment is complete. Charged particles, electric fields and UV light also may be generated by plasma. The ionized gases generally last for very short periods of time (e.g., less than a second), but free radicals and reactive oxygen and nitrogen species that are electrically neutral may last long enough to be effective—perhaps up to many meters away from the source—in destroying fungus, bacteria and their spores. These free radicals denature critical lipid, protein and nucleic acid contents of the microbes, ultimately causing cell death. Research has demonstrated the effectiveness of plasma gas as well as nitrogen and oxygen free radicals such as ozone or hydrogen peroxide vapor or a combination of these in causing retarded fungal growth and fungal death. The byproduct of the plasma process is water ($H_2O$) and carbon dioxide ($CO_2$). Kogelschatz and co-workers have performed early studies on the discharge characteristics and chemistry of air DBDs. More recently Y. Sakiyama et al. created a plasma chemistry model of a SMD device to determine the dynamics of the reactive neutral species it produces.

The non-thermal plasma gas effluent may be directed to a treatment site in two ways: direct mode or indirect mode. Direct mode (see FIG. 4) puts the treatment area within the visible plasma region discharge or plume, which may be between about 0.0 mm and about 5.0 mm for most devices. In direct mode, UV light, some charged particles and electric fields, in addition to reactive neutral species, may directly reach the treatment surface 160, to which a perfluorocarbon 170 may be applied. Indirect mode may have the treatment surface between about 5.0 mm and about 1.0 meter away. Thus, charged particles and electric field may have dissipated or decayed and may not reach the treatment surface. The indirect mode may benefit from a gas delivery system, wherein the plasma gas effluent may be directed to the treatment surface with tubing, inline fans, connectors, ports, etc. for input, delivery and output of antimicrobial agent to the treatment surface. That is, simple diffusion or forced air flow may promote delivery of reactive species to the nail bed, where the non-thermal plasma effluent or gas composition acts as an antimicrobial agent.

Treatment may occur for a predetermined or desired period of time. The antimicrobial agent may be applied for a sufficient time to achieve an effective killing of all or a portion of the fungus within the nail structure. For example, a sufficient time for application may be a time from about 10 seconds to about 4 hours. In one exemplary embodiment, antimicrobial agent may be applied for a time from about 1 minute to about 15 minutes. In yet another exemplary embodiment, antimicrobial agent may be applied for a time from about 5 minutes to about 20 minutes. In a further exemplary embodiment, antimicrobial agent may be applied for a time from about 30 minutes to about 1 hour. In other exemplary embodiments, the application of antimicrobial agent may be cyclical in nature, wherein an electrical control circuit cycles the device on and off, e.g., for a predetermined period of time (for example a 50% duty cycle (1 minute on/1 minute off) for a 30 minute to 1 hour treatment period).

Gaseous Species

Other reactive gases not created by a non-thermal plasma generator may be useful in making redox gas solutions. Such other reactive gases may include any gas capable of directly causing or actively triggering a reaction that eradicates pathogens within or on the surface of a material (e.g., skin or nail) where the gas is also readily soluble in a perfluorocarbon fluid. Such gases include, for example, methanethiol, bromine, chlorine, nitric oxide, ozone, chlorine dioxide, and/or sulfur dioxide. Reactive oxygen and reactive nitrogen species play a central role in oxidation-reduction biochemistry (also called redox biology) and are active in the immune response of both animals and plants. The reactive oxygen/nitrogen/chlorine/bromine or sulfur species listed in Table 1 may be useful in making redox gas solutions.

TABLE 1

List of various reactive oxygen, nitrogen, halogen and sulfur species [10, 22, 23].

| Radical | Non-radical | Radical | Non-radical |
|---|---|---|---|
| Reactive oxygen species (ROS) | | Reactive nitrogen species (RNS) | |
| Superoxide, $O_2^-$ | $H_2O_2$ | Nitric oxide, NO | Nitrous acid, $HNO_2$ |
| Hydroxyl, OH | Ozone $O_3$ | Nitrogen dioxide, $NO_2$ | Nitroxyl cation, $NO^+$ |
| Hydroperoxyl, $HO_2$ | Singlet oxygen ($O_2$ 1 Dg) | Nitrate radical, $NO_3$ | Nitroxyl anion, $NO^-$ |
| Carbonate, $CO_3^-$ | Hypobromous acid, HOBr | | Dinitrogen trioxide, $N_2O_3$ |
| Peroxyl $RO_2$ | Hypochlorous acid, HOCl | | Dinitrogen tetroxide, $N_2O_4$ |
| Alkoxyl, RO | | | Dinitrogen pentoxide, $N_2O_5$ |
| Carbon dioxide radical $CO_2^-$ | Hypoiodous acid, HOI | | Alkyl peroxynitrites, ROONO |
| Singlet ($^2O_2$) | Organic peroxides, ROOH | | Alkyl peroxynitrates, $RO_2ONO$ |
| | Peroxynitrite, ONOO— | | Nitryl chloride, $NO_2Cl$ |
| | Peroxynitrate, $O_2NOO$— | | Peroxyacetyl nitrate, $CH_3C(O)OONO_2$ |
| | Peroxynitrous acid, ONOOH | | |
| | Peroxomonocarbonate, $HOOCO_2^-$ | | |
| | Carbon monoxide, CO | | |
| Reactive chlorine/bromine species | | Reactive sulfur species | |
| Atomic chlorine, Cl | | Thiyl radical S. | Hydrogen sulfide, $H_2S$ |
| Atomic Bromine, Br | Chloramines | | Disulfide, RSSR |
| | Chlorine gas, $Cl_2$ | | Disulfide-S-monoxide, RS(O)SR |
| | Bromine gas, $Br_2$ | | Disulfide-S-dixide, $RS(O)2SR$ |
| | Bromine chloride BrCl | | Sulfonic acid, RSOH |
| | Chlorine dioxide, $ClO_2$ | | Thiol/sulfide, RSR' |

Graves RONS Review Paper 2012

Redox gases can be purchased in their gaseous form but, due to their relatively high vapor pressure, require expensive sealed and pressurized tanks for storage. To provide handling convenience and cost-effectiveness, redox reagents are often created in an aqueous solution such as hypochlorous acid (generated from sodium hypochlorite), hydrogen peroxide, or nitric acid. These aqueous solutions are, however, less reactive than their gaseous counterparts, often requiring elevated temperatures and significant time to complete the redox reaction in situ.

A redox gas may be added to a perfluorocarbon liquid by any conventional technique (e.g., sparging or gas injection or simple diffusion) to create a redox gas solution. Such redox gas solutions provide a means for delivering a stable solution of an oxidation or reduction gas in its most active, non-hydrolyzed state that also allows handling convenience and cost-effectiveness.

Effective treatment of fungal nail infection may come from combining a redox gas with a perfluorocarbon liquid, then applying the redox gas solution topically, so that it penetrates the nail plate and inactivates pathogens residing in the nail bed.

A method for treating nail fungus may comprise the steps of: preparing a redox gas solution and applying the redox gas solution to the infected nails. An applicator may be used to coat the infected nail.

Figure 3A:
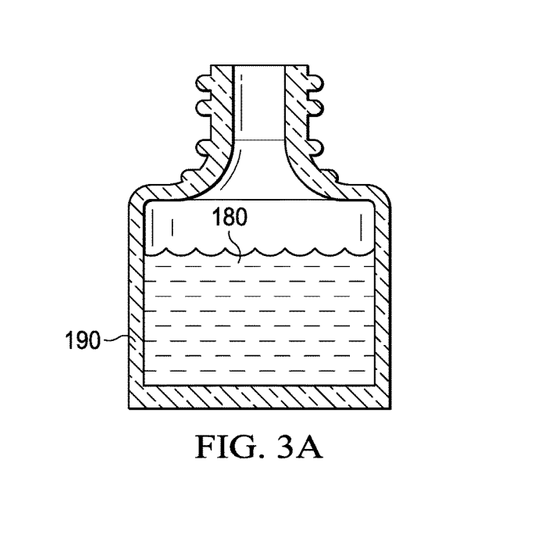
FIG. 3A is a cross-sectional view of a container including an exemplary perfluorocarbon liquid in accordance with the disclosure.
Figure 3B:
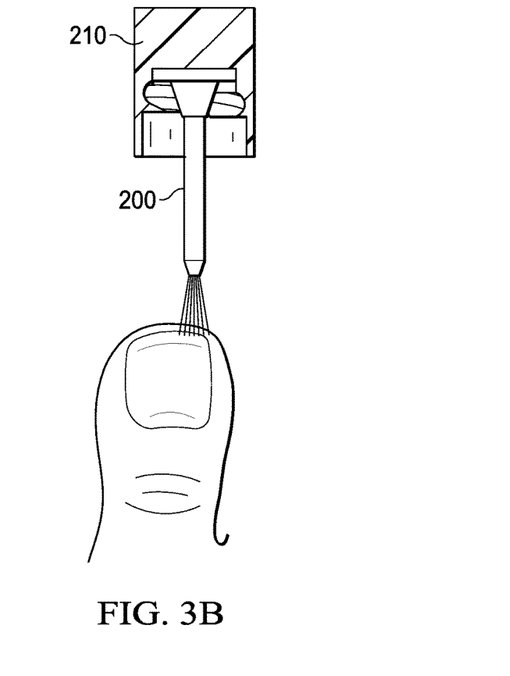
FIG. 3B is a cross-sectional view of a cap for the container shown in FIG. 3A, the cap including an applicator for providing perfluorocarbon liquid to a nail/tissue.
Figure 3C:
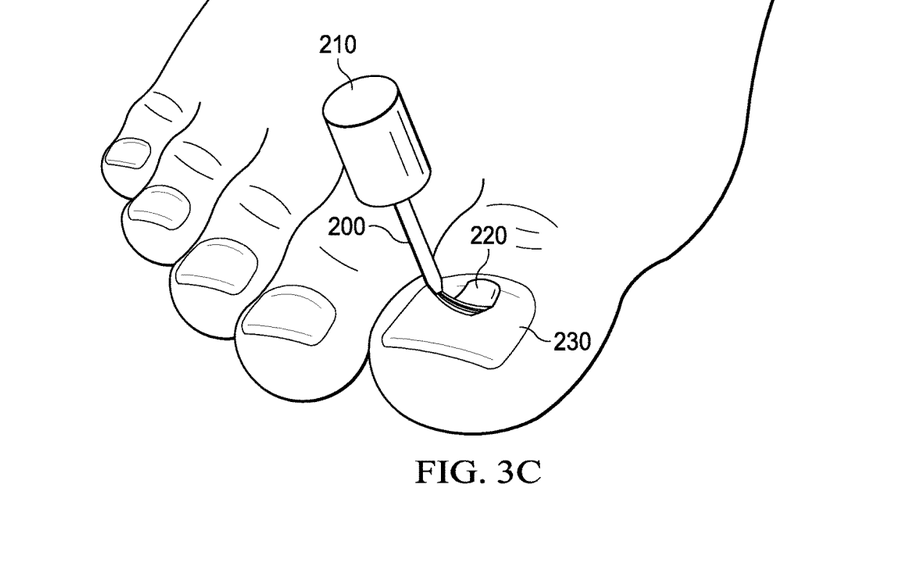
FIG. 3C is a perspective view of an exemplary application of perfluorocarbon liquid to nail/tissue using the applicator shown in FIG. 3B.

As shown in FIGS. 3A-3C, in one exemplary embodiment, a redox gas solution 180 may include chlorine dioxide gas dissolved in perfluorodecalin to saturation and may be provided in a container 190 as a topical treatment for onychomycosis. The solution may have a minimum of 80 ppm chlorine dioxide as the treating agent. Treating an infected nail with the solution comprises using an applicator 200 (for example coupled to the cap 210 of container 190) to spread a coating 220 on and around the nail 230. In one embodiment, such application includes a series of successive treatments to improve the aesthetic appearance of the nail, destroy the fungal infection and promote healthy nail growth. In another embodiment, the solution may be applied once a day for a minimum of sixty days to inactivate the fungus. In another embodiment, the solution may be applied once a week to prevent fungus or fungal spores from reinfecting the nail matrix.

A redox gas solution alternately may be generated at the skin or nail site by applying a perfluorocarbon liquid topically to the treatment area then treating the site with a redox gas, such as a gas created by a plasma-generating device. See FIGS. 2 and 4. As an example, a perfluorocarbon liquid may be administered immediately prior to treatment with a non-thermal plasma device in an amount sufficient to enhance the permeation of antifungal gas through and around the nail. The non-thermal plasma device allows the in-situ generation of gaseous reactive oxygen species and reactive nitrogen species that have antifungal properties.

Figure 5A:
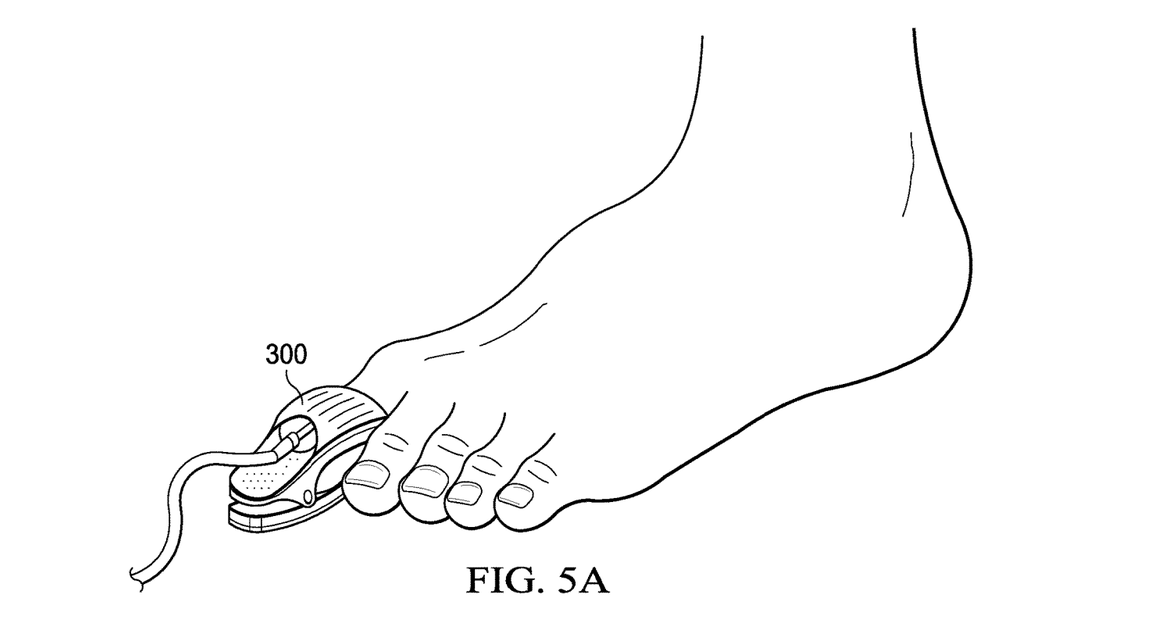
FIG. 5A is a perspective view of an exemplary toe-clip applicator in accordance with the disclosure.
Figure 5B:
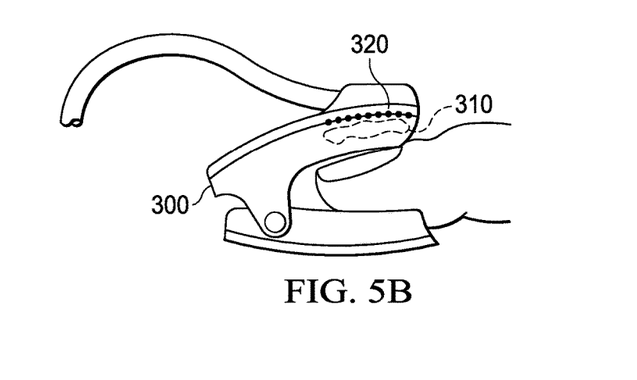
FIG. 5B is a partial cross-sectional view of the exemplary toe-clip applicator shown in FIG. 5A.

In one embodiment, perfluorodecalin is pre-applied to the infected nail to act as a redox gas facilitator substance. As shown in FIGS. 5A and 5B, a toe-clip 300 incorporating a plasma-generating device 320 is then attached to the infected toe and a 30-minute treatment protocol is initiated which generates antifungal gases 310 using electrical energy and air. This treatment may be performed as a series of successive treatments to improve the aesthetic appearance of the nail, destroy the fungal infection and promote healthy nail growth. The perfluorodecalin enhances the gas exchange between the nail bed and the plasma-generating device and allows the antifungal gas to more effectively penetrate the dense nail plate.

Figure 6:
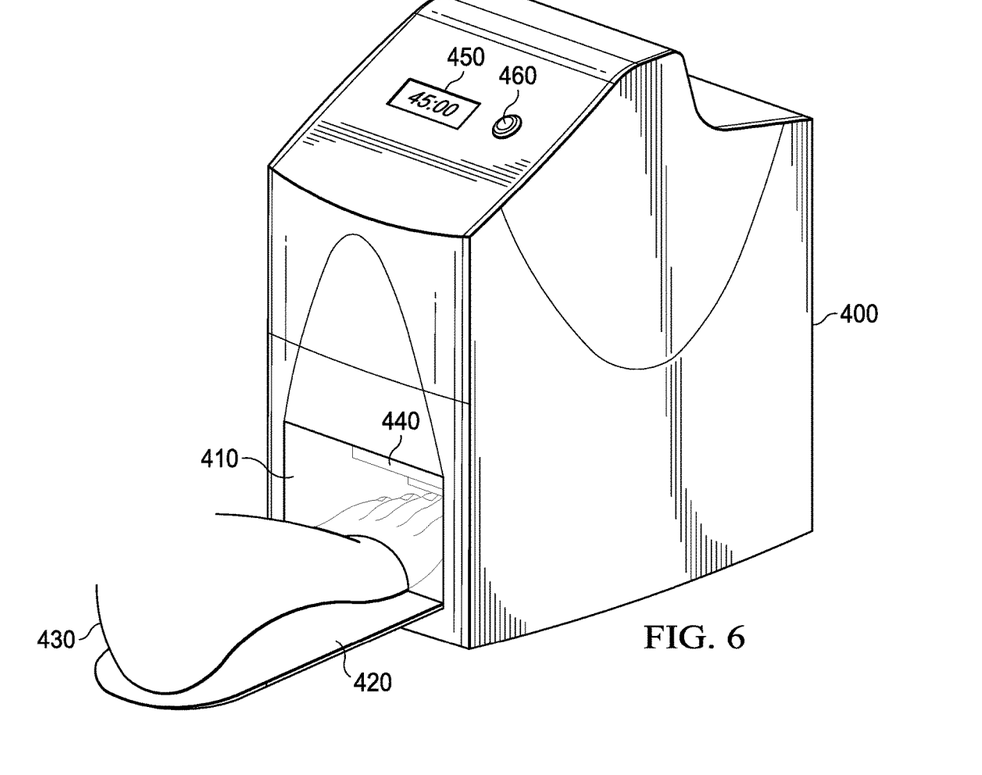
FIG. 6 is a perspective view of an alternate exemplary treatment system embodiment in accordance with the disclosure.

In another exemplary embodiment, a pre-made redox gas solution may be applied to a treatment area and additional treatment can be applied through the use of a non-thermal plasma treatment, thus replenishing or adding additional species of redox gas to the treatment area. As shown in FIG. 6, a plasma-generating device 400 may include a chamber 410 having a lid or door 420, within which chamber a foot 430 may be placed for treatment proximate a plasma source 440. The plasma may be provided for a predetermined amount of time using a control circuit including a timer 450 that is activated by pressing a start/stop button or switch 460.

In another exemplary embodiment, the method includes coating the affected nail(s) along with the entire foot, in order to destroy pathogens thereon and help prevent reinfection of the nail by pathogens residing elsewhere on the foot.

The redox gas solutions used during treatment may provide a means for delivering a stable solution of an oxidation or reduction gas in its most active, non-hydrolyzed state. In addition, the redox gas solutions may offer the advantage of providing a very low surface tension medium (generally on the order of approximately 15 dynes/cm), thereby enabling the oxidizing gas solution to efficiently contact and thoroughly penetrate a nail or skin infection.

Additionally, the PFC can act as a gas facilitator by providing an improvement in gas exchange between a non-thermal plasma device that creates in situ an antimicrobial gas and the nail barrier where the microbe resides. The PFC enhances the capacity of an active fungicidal gas to effectively penetrate the keratin matrix of fingernails and toenails such as to produce therapeutically relevant concentrations even in deeper regions of the matrix.

Examples

The following examples are offered to aid in a better understanding of the present invention. These examples are not to be construed as an exhaustive compilation of all embodiments of the present invention and are not to be construed as limiting the scope thereof.

Eradication of *T. rubrum* Through a Bovine Hoof Using Perfluorodecalin (PFD) Facilitator and an SMD Plasma-Generating Device.

The in vitro test model uses a bovine hoof disk, a surrogate nail model established in the literature. It is used along with a modified Franz-type diffusion cell to isolate the fungal contaminated side of the hoof in an enclosed chamber that ensures the treatment path is through the hoof barrier. An equal amount of *T. rubrum* is pipetted onto each hoof disc consisting of a 100 ul suspension. Each hoof disk is then placed fungus side down into the modified Franz cell and sealed with an O-ring. Each hoof is then plasma treated for 45 minutes where the average thickness of hoof disks is 0.35 mm. Eight hoof disks were treated as:

a. Control that is placed directly into the wash tube without any treatment.

b. Two PFD-only hoofs had 100 ul PFD pipetted directly onto the hoof opposite side from the fungus. This was allowed to sit for 45 minutes in the hood before placing in the wash tube.

c. Two Plasma treatment only hoofs get just a 45 minute plasma treatment.

d. Three Plasma treatment with PFD hoofs had 100 ul PFD pipetted directly onto the hoof opposite side from the fungus immediately before applying plasma treatment (i.e., while wet).

After treatment, each hoof went through a fungal collection protocol consisting of washing, dilution, plating and incubation. The results after seven days of incubation was a colony count of about 24,000,000 from the control hoof plate. The two hoofs that were treated with PFD-only had colony reductions of 7% and 28% compared to control. The two hoofs that were treated with 45 minutes of plasma only had colony reductions of 84% and 88% when compared to control and quite unexpectedly the three hoofs that were treated with both PFD and 45 minutes of plasma treatment showed a colony reduction of 94% for one hoof and no colonies or 100% and 100% reductions for the other two hoofs.

Application of PFC onto the Skin/Nail

The contacting of the infected area with the perfluorocarbon can occur by various means. The perfluorocarbon can be applied with a dropper, foam tip swab, a cotton tip swab or a sponge applicator. It may be sprayed or squeezed on in a foam or gel formulation.

A further apparatus for contacting the infected area with a perfluorocarbon consist of a gas-permeable membrane that includes perfluorocarbon liquid in its composition and allows for the rapid, enhanced and uniform transfer of plasma reactive species between the plasma device and the infection. The contacting of the infection with the perfluorocarbon membrane (e.g., a dressing, bandage, patch, etc.) may define the treatment site. The gas permeable membrane composition comprises at least one material selected from ceramics, polymers, woven substrates, non-woven substrates, polyamide, polyester, polyurethane, fluorocarbon polymers, polyethylene, polypropylene, polyvinyl alcohol, polystyrene, vinyl, plastics, metals, alloys, minerals, non-metallic minerals, wood, fibers, cloth, glass, and hydrogels. In one embodiment, the membrane barrier is a silicone composition that contains an effective amount of perfluorocarbon and acts as a dressing. For nail treatment, the membrane may be manufactured in a toe or finger cot shape that may be slipped easily over the infected digit.

Loading PFC with Antifungal Gas

A PFC may be loaded with antifungal gas in a manufacturing facility. Alternately, a home-use device may be provided so that a patient may "load" the PFC at their home, then apply it to their toenails. The loading can be done with a plasma device, and/or a pure gas canister (NO, ozone, $H_2O_2$, etc.), etc. before treatment application by the patient at home. As described, there are other ways of loading the PFC with antifungal gas after it is applied to the infections site (e.g., besides a plasma device). In one embodiment, a pure gas canister (NO, ozone, $H_2O_2$, etc.) may be used. In another embodiment, a secondary chemical reaction may create the gas. Redox gases can be purchased in their gaseous form but have relatively high vapor pressure, require expensive sealed and pressurized tanks for storage. To provide handling convenience and cost-effectiveness, redox reagents are often created in an aqueous solution such as hypochlorous acid (generated from sodium hypochlorite), hydrogen peroxide, or nitric acid. These aqueous solutions are, however, less reactive than their gaseous counterparts, often requiring elevated temperatures and significant time to complete the redox reaction in situ.

Again, a redox gas may be added to a perfluorocarbon liquid by any conventional technique (e.g., sparging or gas injection or simple diffusion) to create a redox gas solution. Such redox gas solutions provide a means for delivering a stable solution of an oxidation or reduction gas in its most active, non-hydrolyzed state that also allows handling convenience and cost-effectiveness.

Sterilization and Other Therapies

Use of the described system and method also may promote wound sterilization and healing, may treat ear infections, may improve the sterilization of medical devices, may treat dental infections, may treat acne and various other dermatological infections, may promote bleeding cessation, may improve hand disinfection hygiene, or may treat skin, esophagus or colon cancer. It can also be used in veterinarian animal health for all such described applications.

In one embodiment, a method of sterilizing or decontaminating an item comprises the steps of: (a) coating the item to be sterilized with a perfluorocarbon liquid layer to allow the perfluorocarbon liquid to come in close proximity with the item; (b) generating a gaseous plasma around the item, such that both the liquid perfluorocarbon and the exterior of item is exposed to reactive components of said plasma; and (c)

maintaining the item in said plasma for a time period sufficient to allow the active sterilizing species generated from the plasma to effect sterilization and destroy any microorganisms present.

In another embodiment, decontamination of a liquid or gas may occur using a PFC including a reactive species. Examples include, without limitation, using the PFC/reactive species solution to eliminate microbes in blood with the aid of a dialysis machine, and to improve the sterilization of air using conventional methods.

It should be understood that the foregoing description is only illustrative of the invention. Various alternatives and modifications can be devised by those skilled in the art having the benefit of this disclosure, without departing from the invention. Accordingly, the invention is intended to embrace all such alternatives, modifications and variances.

Certain exemplary embodiments of the disclosure may be described. Of course, the embodiments may be modified in form and content, and are not exhaustive, i.e., additional aspects of the disclosure, as well as additional embodiments, will be understood and may be set forth in view of the description herein. Further, while the invention may be susceptible to various modifications and alternative forms, specific embodiments have been shown by way of example in the drawings and will be described in detail herein. However, it should be understood that the invention is not intended to be limited to the particular forms disclosed. Rather, the invention is to cover all modifications, equivalents and alternatives falling within the spirit and scope of the invention.

We claim:

1. A method of treating nails or tissues infected with a microbial infection comprising:
    a) Contacting a nail or tissue portion infected with a microbial infection with a gas-permeable membrane, wherein the membrane comprises a carrier fluid consisting of a perfluorocarbon (PFC) fluid;
    b) Placing the infected nail or tissue in contact with said gas-permeable membrane and PFC fluid in an enclosed chamber;
    c) Positioning a plasma-generating device within the enclosed chamber, wherein the plasma device comprises a high voltage electrode, a dielectric and a ground electrode;
    d) Said plasma-generating device connected to a timer;
    e) Setting said timer to a period or plurality of cycling times selected from the range consisting of a minimum of 10 seconds and about 135 minutes;
    f) Starting said timer;
    g) Energizing the plasma-generating device with electricity to form an in air redox gaseous reactive-species, which dissolves in and forms a redox gas solution delivered within the PFC fluid, wherein said redox gaseous-reactive species consists of one or more gaseous plasma components, dissolves in and forms a redox gas solution delivered within the PFC fluid in contact with the gas-permeable membrane;
    h) Said redox gas solution penetrating into said infected nail or tissue, wherein the redox gas solution enhances the capacity of an active fungicidal gas to effectively penetrate the keratin matrix of fingernails, toenails and tissues to produce therapeutically relevant concentrations of fungicidal gas into deeper regions of the matrix;
    i) Said redox gas solution contacting the infected nail or tissue for said period or plurality of cycling times treats the microbial infection and destroys all or a portion of the microbial infection residing in the microbial infected nail or tissue.

2. The method as described in claim 1, wherein the redox gaseous reactive species is one or more of reactive oxygen, reactive nitrogen, reactive chlorine, reactive bromine, and reactive sulfur species.

3. The method as described in claim 1, wherein the high voltage electrode comprises a copper block in communication with a quartz plate, said quartz plate being in communication with a wire mesh.

4. The method as described in claim 1, wherein the wire mesh is the ground.

5. The method as described in claim 1, wherein the redox gas is generated by a non-thermal plasma device.

6. The method as described in claim 1, wherein the plasma-generating device is selected from the group consisting of a non-thermal plasma device that forms a corona discharge plasma, a dielectric barrier discharge plasma, a surface micro-discharge plasma, an inductively coupled plasma, a microwave induced plasma, a plasma jet, and a capacitively coupled radio frequency induced plasma.

7. The method as described in claim 1, wherein the microbial infected nail or tissue portion includes a digit or foot portion.

8. The method as described in claim 1, wherein the perfluorocarbon fluid is provided in a form selected from the group consisting of: liquid, nebulized, vaporized and aerosolized liquid phase, emulsion, foam and gel.

9. The method of claim 1, wherein said infected nail or tissue portion includes an onychomycosis infection.

10. The method of claim 1, wherein the treatment of said microbial infected nail or tissue treats an animal or human body part comprising a disease and/or a wound.

11. The method of claim 1, wherein said microbial infected nail or tissue body part is exposed to a plasma discharge for a time between about 30 minutes to 1 hour.

12. The method of claim 1, wherein said gas-permeable membrane consists of one or more materials selected from the group consisting of: silicone polymers, polyamide, polyester, polyurethane, fluorocarbon polymers, polyethylene, polypropylene, polyvinyl alcohol, polystyrene, vinyl, plastics, metals, alloys, minerals, non-metallic minerals, wood, fibers, cloth, glass, and hydrogels.

13. The method according to claim 1, wherein the perfluorocarbon fluid is selected from the group consisting of: liquid, nebulized, vaporized and aerosolized liquid phase, emulsion, foam and gel.

14. The method according to claim 1, wherein the PFC liquid is selected from the group consisting of perfluorodecalin, perfluoropentane, perfluorohexane, perfluoroheptane, perfluorooctane, perfluoromethylcyclohexane, perfluorotributyl amine, perfluorotriamyl amine, perfluoro-N-methylmo.phi.holine, perfluoro-Nethylmo.phi.holine, perfluoroisopropyl mo.phi.holine, perfluoro-N-methyl pyrrolidine, perfluoro-1,2 is(trifluoromethyl)hexafluorocyclobutane, perfluoro-2-butyltetrahydrofuran, perfluorotriethylamine, perfluorodibutyl ether, and mixtures thereof.

15. The method of claim 9, wherein the onychomycosis infection is caused by a pathogen selected from the group consisting of dermatophytes, *Candida*, and non-dermatophytic molds.

16. The method of claim 15, wherein the dermatophyte is selected from the group consisting of *Trichophyton rubrum, T. interdigitale, T. violaceum, T. tonsurans*, and *T. soudanense, Epidermophyton floccosum*, and *Microsporum gypseum*.

17. The method of claim 11, wherein the plasma discharge (antimicrobial agent) cycles 1-minute ON/1 minute OFF for a 30 minute to a 1 (one) hour treatment period, including periods and intervals therein.

18. A method of treating a nail or tissue portion infected with one or more microbial diseases comprising:
   a) Coating a nail or a tissue infected area with a "gas" carrier consisting of a perfluorocarbon (PFC) fluid;
   b) Placing the infected nail or tissue coated with said perfluorocarbon fluid in an enclosed chamber;
   c) Positioning a plasma-generating device within the enclosed chamber, wherein the plasma device comprises a high voltage electrode, a dielectric and a ground electrode consisting of a wire mesh, wherein the plasma-generating device is connected to a timer;
   d) Setting said timer to a period or plurality of cycling times selected from the range consisting of a minimum of 10 seconds and about 135 minutes;
   e) Starting said timer;
   f) Energizing the plasma-generating device with electricity to form an in air redox gaseous reactive species for said period or said plurality of cycling times, which dissolves in and forms a redox gas solution delivered within the PFC fluid, wherein said redox gaseous reactive species consists of one or more gaseous plasma components, and wherein said perfluorocarbon fluid in contact with said redox gas solution penetrates into the nail or tissue is in communication with said reactive species;
   g) Dissolving the redox gaseous reactive species in the perfluorocarbon fluid, coating the nail or tissue infected area, forming a redox gas solution;
   h) Transferring the redox gas solution in contact with said nail or tissue into said infected nail or tissue;
   i) Contacting the redox gas solution to permit contact and penetration of reactive species into the nail or tissue to destroy all or a portion of one or more microbial disease pathogens residing in the infected nail or tissue.

19. The method as described in claim 18, wherein the redox gaseous reactive species is one or more of reactive oxygen, reactive nitrogen, reactive chlorine, and reactive sulfur species.

20. The method as described in claim 18, wherein the high voltage electrode comprises of a copper block in communication with a quartz plate and wherein said quartz plate is in communication with the wire mesh.

21. The method as described in claim 18, wherein said ground electrode consists of stainless-steel woven wire mesh.

22. The method as described in claim 18, wherein the redox gas is generated by a non-thermal plasma device.

23. The method as described in claim 18, wherein the said plasma-generating device is selected from the group consisting of a non-thermal plasma device that forms a corona discharge plasma, a dielectric barrier discharge plasma, a surface micro-discharge plasma, an inductively coupled plasma, a microwave induced plasma, a plasma jet, or a capacitively coupled radio frequency induced plasma.

24. The method as described in claim 18, wherein said nail or tissue portion includes a digit or a foot portion.

25. The method according to claim 18, wherein the PFC liquid is selected from the group consisting of perfluorodecalin, perfluoropentane, perfluorohexane, perfluoroheptane, perfluorooctane, perfluoromethylcyclohexane, perfluorotributyl amine, perfluorotriamyl amine, perfluoro-N-methylmo.phi.holine, perfluoro-Nethylmo.phi.holine, perfluoroisopropyl mo.phi.holine, perfluoro-N-methyl pyrrolidine, perfluoro-1,2 is(trifluoromethyl)hexafluorocyclobutane, perfluoro-2-butyltetrahydrofuran, perfluorotriethylamine, perfluorodibutyl ether, and mixtures thereof.

26. The method of claim 18, wherein said infected nail or tissue portion includes an onychomycosis infection.

27. The method of claim 18, wherein the treatment of said microbial infected nail or tissue treats an animal or human body part comprising a disease and/or a wound.

28. The method of claim 18, wherein said microbial infected nail or tissue body part is exposed to a plasma discharge for a time between about 30 minutes to 1 hour.

* * * * *